United States Patent
Toyoda et al.

(10) Patent No.: US 8,316,532 B2
(45) Date of Patent: Nov. 27, 2012

(54) METHOD OF PRODUCING A WIRED CIRCUIT BOARD

(75) Inventors: Yoshihiro Toyoda, Osaka (JP); Terukazu Ihara, Osaka (JP)

(73) Assignee: Nitto Denko Corporation, Osaka (JP)

( * ) Notice: Subject to any disclaimer, the term of this patent is extended or adjusted under 35 U.S.C. 154(b) by 255 days.

(21) Appl. No.: 12/662,109

(22) Filed: Mar. 31, 2010

(65) Prior Publication Data

US 2010/0263206 A1 Oct. 21, 2010

(30) Foreign Application Priority Data

Apr. 15, 2009 (JP) ................... 2009-099198

(51) Int. Cl.
*H05K 3/00* (2006.01)
(52) U.S. Cl. ............... 29/829; 29/830; 29/831; 29/832; 29/852; 29/854
(58) Field of Classification Search ............ 29/829, 29/830, 848, 852, 854, 831, 832; 174/250, 174/255, 258, 257; 257/13, 21, 53, 82, 83, 257/95; 361/39, 40, 117, 173, 174, 176, 361/177; 216/13, 66
See application file for complete search history.

(56) References Cited

U.S. PATENT DOCUMENTS

| 4,970,368 | A | * | 11/1990 | Yamazaki et al. ....... 219/121.85 |
| 6,084,664 | A | * | 7/2000 | Matsumoto et al. ....... 356/237.4 |
| 2009/0114426 | A1 | * | 5/2009 | Tsunekawa et al. .......... 174/250 |

FOREIGN PATENT DOCUMENTS

| JP | 11-307883 | 11/1999 |
| JP | 2006-112845 | 4/2006 |
| JP | 2008-153595 | 7/2008 |

* cited by examiner

*Primary Examiner* — Derris Banks
*Assistant Examiner* — Tai Nguyen
(74) *Attorney, Agent, or Firm* — Jean C. Edwards, Esq.; Edwards Neils PLLC

(57) ABSTRACT

A producing method of a wired circuit board includes the steps of preparing the wired circuit board, placing the wired circuit board on a support table, and applying light from above the wired circuit board toward the wired circuit board, and sensing pattern reflected light, table reflected light and foreign-matter reflected light to inspect the conductive pattern and the foreign matter based on a contrast therebetween. In the step of inspecting the conductive pattern and the foreign matter, a reflectance of the table reflected light is in a range of 25 to 55%, and a reflectance of the foreign-matter reflected light is in a range of not more than 10%.

4 Claims, 6 Drawing Sheets

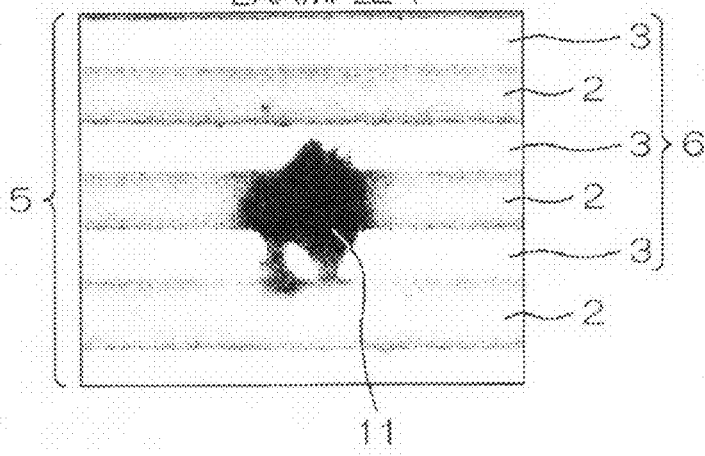
FIG.6 EXAMPLE 1
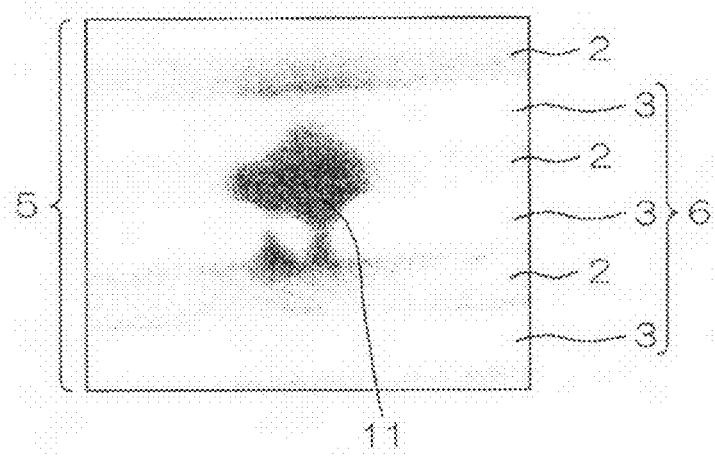
FIG.7 EXAMPLE 2
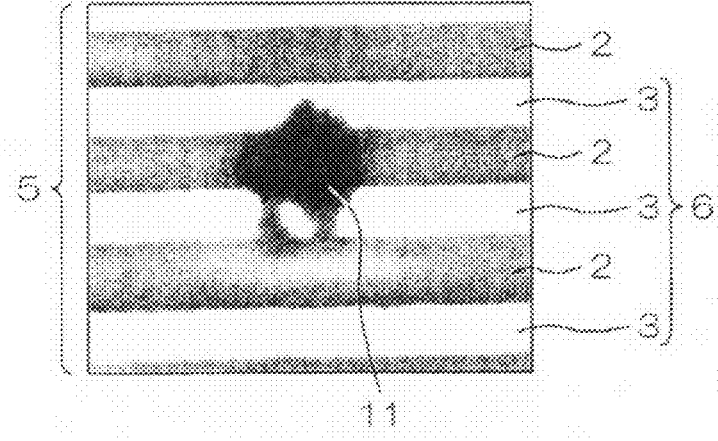
FIG.8 EXAMPLE 3

FIG.9 COMPARATIVE EXAMPLE
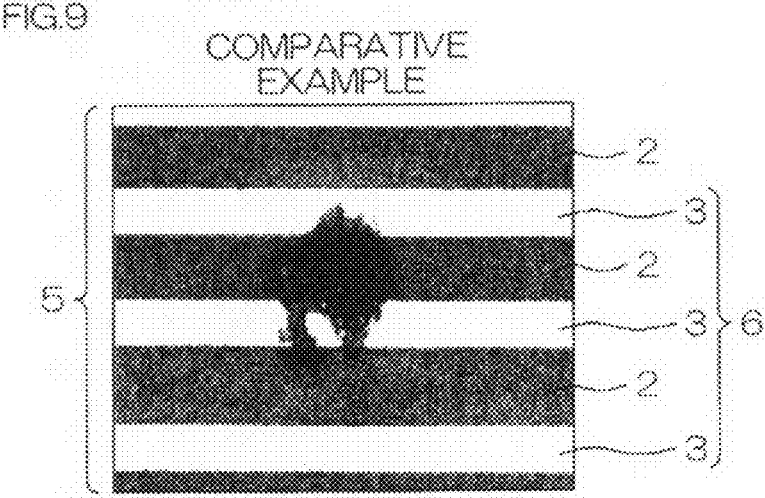
FIG.10 COMPARATIVE EXAMPLE 2
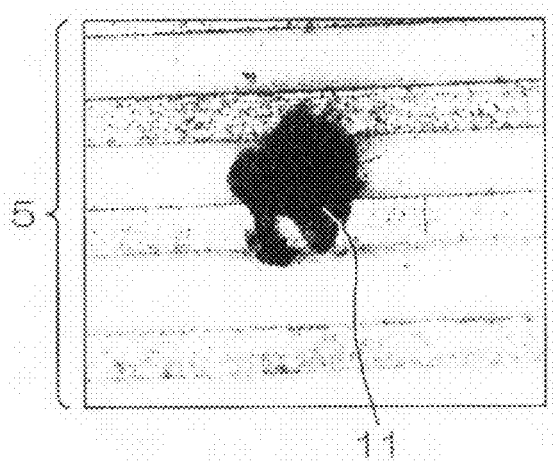
FIG.11 COMPARATIVE EXAMPLE 3
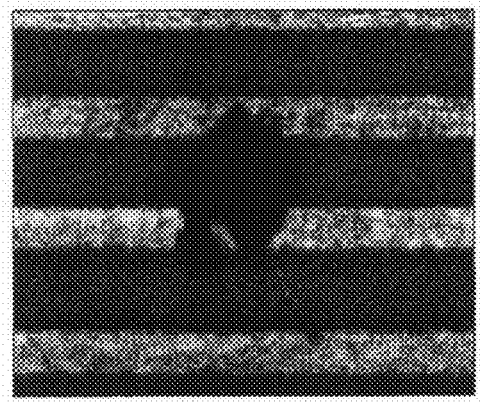

METHOD OF PRODUCING A WIRED CIRCUIT BOARD

CROSS-REFERENCE TO RELATED APPLICATIONS

This patent application priority from Japanese Patent Application No. 2009-099198, filed on Apr. 15, 2009, the contents of which are herein incorporated by reference in their entirety.

BACKGROUND OF THE INVENTION

1. Field of the Invention

The present invention relates to a producing method of a wired circuit board and, more particularly, to a producing method of a wired circuit board such as a flexible wired circuit board.

2. Description of the Related Art

A wired circuit board such as a flexible wired circuit board has an insulating base layer, a conductive pattern formed thereon, and an insulating cover layer formed on the insulating base layer so as to cover the conductive pattern. It has been known that, in the production of such a wired circuit board, an insulating base layer, a conductive pattern, and an insulating cover layer are successively formed, and then the shape of the conductive pattern is optically inspected for a defect.

For example, as shown in FIG. 5, it has been proposed that a wired circuit board 40 including an insulating base layer 42, a conductive pattern 41, and an insulating cover layer 45 is placed on the upper surface of a support table 44 made of metal, and then light is applied to the wired circuit board 40 from thereabove to conduct an inspection of the conductive pattern 41 with reflected light which is the light reflected by the wired circuit board 40 (see, e.g., Japanese Unexamined Patent No. 2006-112845).

Specifically, pattern reflected light 51 which is the light reflected by the conductive pattern 41 via the insulating cover layer 45 and table reflected light 52 which is the light reflected by the support table 44 via the insulating cover layer 45 and the insulating base layer 42 exposed from the conductive pattern 41 are each sensed as the reflected light with a CCD camera.

In the inspection of the conductive pattern 41 described in Japanese Unexamined Patent No. 2006-112845, the difference between an amount of the pattern reflected light 51 and an amount of the table reflected light 52, i.e., the contrast (brightness difference) therebetween is used to recognize the shape of the conductive pattern 41, and determine whether or not the shape of the conductive pattern 41 is defective.

In the inspection of Japanese Unexamined Patent No. 2006-112845, there is the problem that, when the contrast between the pattern reflected light 51 and the table reflected light 52 is low, the shape of the conductive pattern 41 is difficult to recognize. To solve such a problem, it has been proposed that the reflectance of the table reflected light 52 is reduced to a value of not more than 10% to ensure a high contrast between the pattern reflected light 51 and the table reflected light 52.

On the other hand, it has been conventionally proposed that, in the production of a wired circuit board, a foreign matter present on a conductive pattern is inspected (see, e.g., Japanese Unexamined Patent No. 11-307883).

Specifically, as indicated by the solid line of FIG. 5, the reflectance of foreign-matter reflected light 53 which is the light reflected by a foreign matter 46 via the insulating cover layer 45 is low when the foreign matter 46 is made of a resin material such as rubber. Accordingly, the foreign matter 46 present on the conductive pattern 41 is inspected by ensuring a high contrast between the foreign-matter reflected light 53 and the pattern reflected light 51.

SUMMARY OF THE INVENTION

However, as indicated by the imaginary lines of FIG. 5, when the foreign matter 46 is present on the upper surface of the insulating base layer 42 exposed from the conductive pattern 41, each of the foreign-matter reflected light 53 and the table reflected light 52 has a low reflectance so that the contrast therebetween is low. As a result, it is difficult to inspect the foreign matter 46 present on the upper surface of the insulating base layer 42 exposed from the conductive pattern 41.

It is therefore an object of the present invention to provide a producing method of a wired circuit board which allows an inspection of a conductive pattern and an inspection of a foreign matter present on an insulating base layer exposed from the conductive pattern to be performed easily and simultaneously.

A producing method of a wired circuit board, the producing method comprising the steps of: preparing the wired circuit board comprising an insulating base layer, a conductive pattern formed on the insulating base layer, and an insulating cover layer formed on the insulating base layer so as to cover the conductive pattern; placing the wired circuit board on a support table; and applying light from above the wired circuit board toward the wired circuit board, and sensing pattern reflected light which is the light reflected by the conductive pattern via the insulating cover layer, table reflected light which is the light reflected by the support table via the insulating cover layer and the insulating base layer exposed from the conductive pattern, and foreign-matter reflected light which is the light reflected by a foreign matter present on the insulating base layer exposed from the conductive pattern to inspect the conductive pattern and the foreign matter based on a contrast therebetween, wherein, in the step of inspecting the conductive pattern and the foreign matter, a reflectance of the table reflected light is in a range of 25 to 55%, and a reflectance of the foreign-matter reflected light is in a range of not more than 10%.

In the producing method of the wired circuit board of the present invention, it is preferable that a light transmittance of each of the insulating base layer and the insulating cover layer is not less than 60%

In the producing method of the wired circuit board of the present invention, it is preferable that a reflectance of the pattern reflected light is higher than the reflectance of the table reflected light by a value of not less than 20%

In the producing method of the wired circuit board of the present invention, it is preferable that a wavelength of the light is in a range of not less than 500 nm In accordance with the producing method of the wired circuit board of the present invention, in the step of inspecting the conductive pattern and the foreign matter, the reflectance of the table reflected light is in the range of 25 to 55%, and the reflectance of the foreign-matter reflected light is in the range of not more than 10%.

This allows each of the contrast between the pattern reflected light and the table reflected light and the contrast between the table reflected light and the foreign-matter reflected light to be set high in a well-balanced manner.

Therefore, it is possible to easily and simultaneously perform an inspection of the conductive pattern and an inspection of the foreign matter present on the insulating base layer exposed from the conductive pattern.

BRIEF DESCRIPTION OF THE DRAWINGS

FIG. 6 shows an image processed view in an inspection step of EXAMPLE 1;

FIG. 7 shows an image processed view in an inspection step of EXAMPLE 2;

FIG. 8 shows an image processed view in an inspection step of EXAMPLE 3;

FIG. 9 shows an image processed view in an inspection step of COMPARATIVE EXAMPLE 1;

FIG. 10 shows an image processed view in an inspection step of COMPARATIVE EXAMPLE 2; and FIG. 11 shows an image processed view in an inspection step of COMPARATIVE EXAMPLE 3.

DETAILED DESCRIPTION OF THE INVENTION

Figure 1:
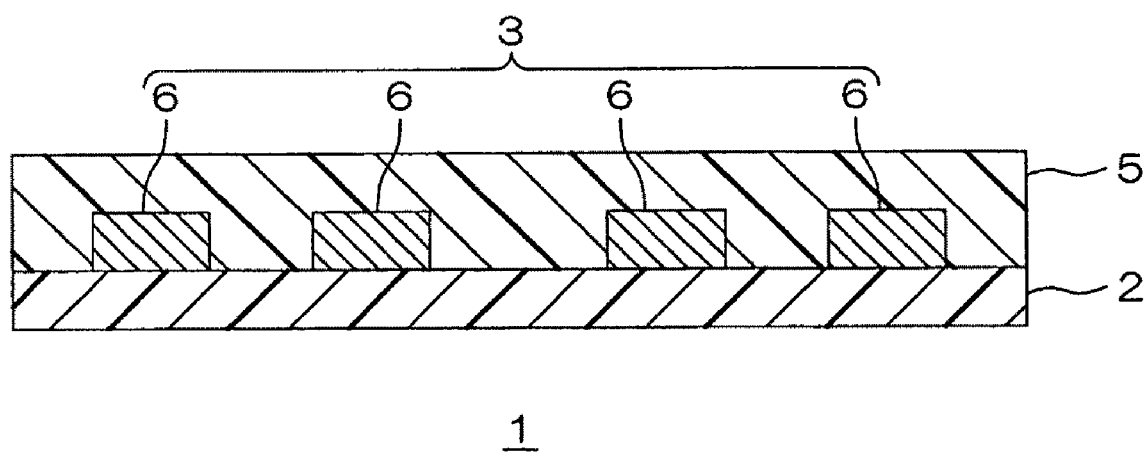
FIG. 1 is a cross-sectional view along a widthwise direction of an embodiment of a wired circuit board produced by a producing method of a wired circuit board of the present invention.
Figure 2:
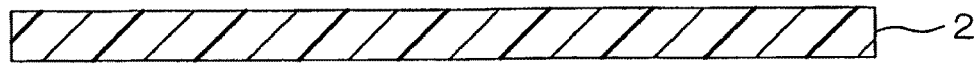
FIG. 2 is a process step view of an embodiment of the producing method of the wired circuit board of the present invention, (a) showing the step of preparing an insulating base layer, (b) showing the step of forming a conductive pattern, (c) showing the step of forming an insulating cover layer, and (d) showing the step of inspecting the conductive pattern and a foreign matter in the wired circuit board in which a foreign matter is not present, and wires are formed normally, or (d') showing the step of inspecting the conductive pattern and a foreign matter in the wired circuit board in which the foreign matter is present, and wires are short-circuited.
Figure 2:
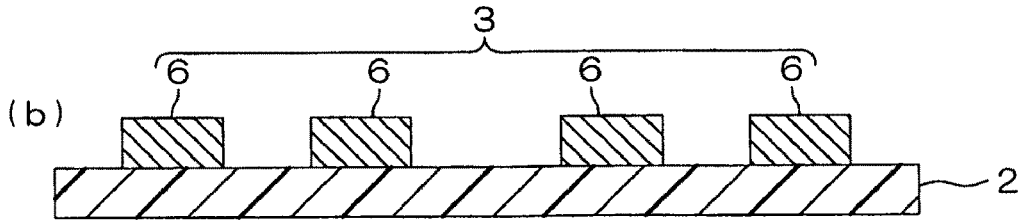
Figure 2:
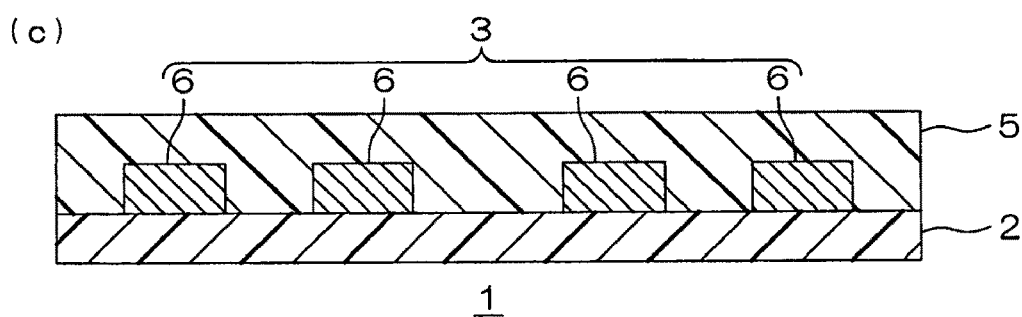
Figure 2:
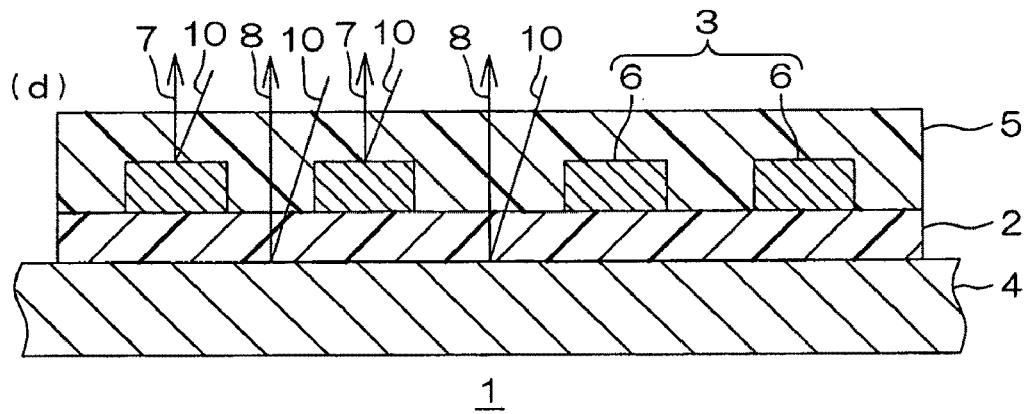
Figure 2:
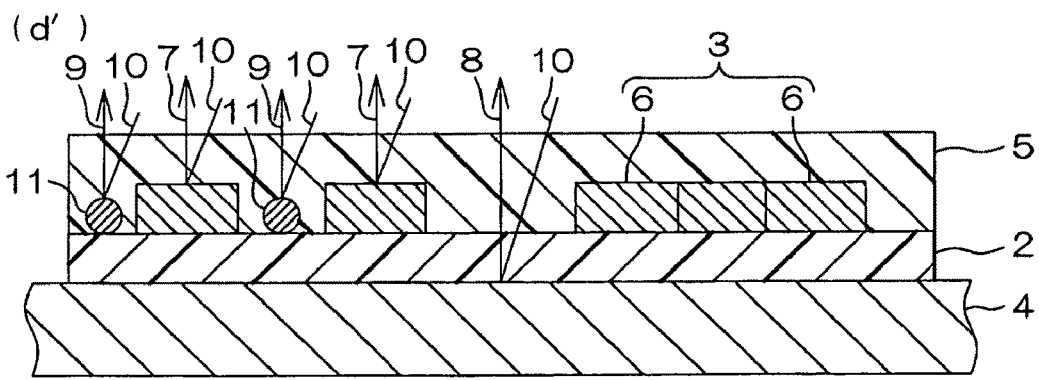
Figure 3:
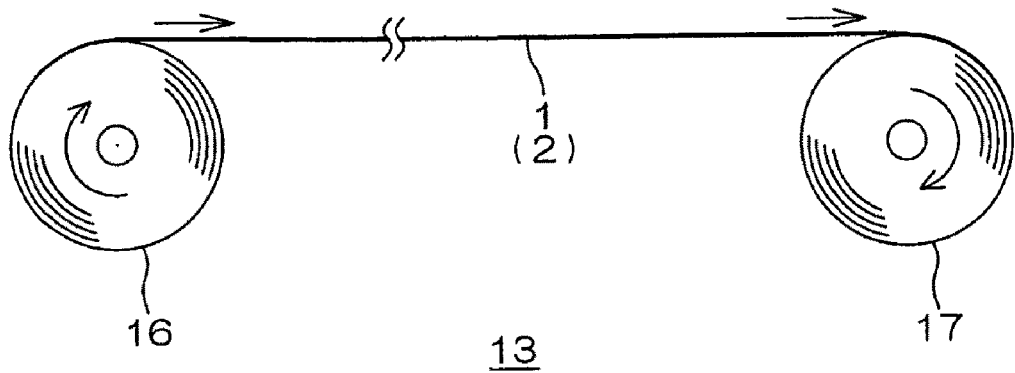
FIG. 3 is a schematic structural view of a conveying device for implementing the embodiment of FIG. 2.
Figure 4:
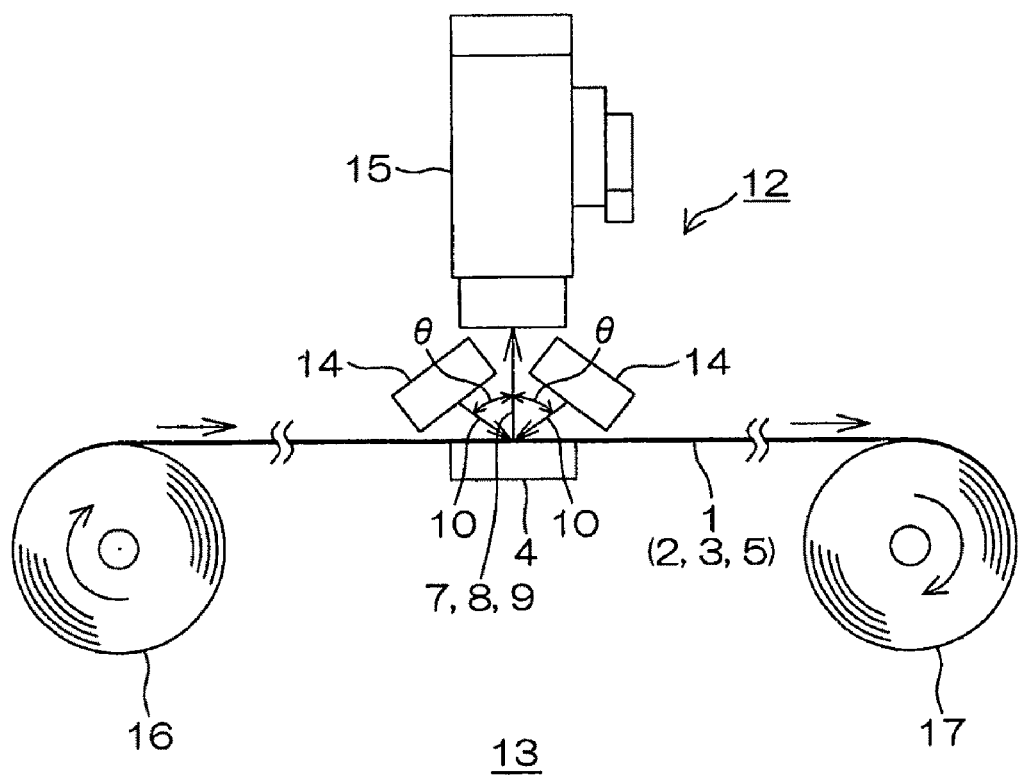
FIG. 4 is a schematic structural view of an inspection device for performing an inspection step.
Figure 5:
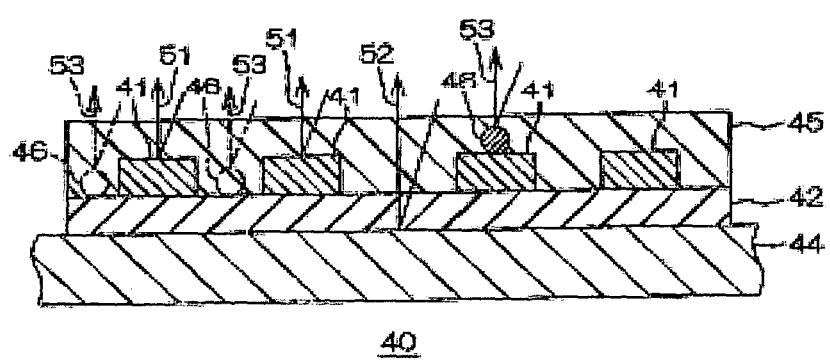
FIG. 5 is an illustrative view of a prior-art technology, showing the step of inspecting a wired circuit board in which a foreign matter is present on a conductive pattern.

FIG. 1 is a cross-sectional view along a widthwise direction (direction perpendicular to a longitudinal direction) of an embodiment of a wired circuit board produced by a producing method of a wired circuit board of the present invention. FIG. 2 is a process step view of an embodiment of the producing method of the wired circuit board of the present invention. FIG. 3 is a schematic structural view of a conveying device for implementing the embodiment of FIG. 2. FIG. 4 is a schematic structural view of an inspection device for performing an inspection step described later.

In FIG. 1, a wired circuit board 1 is a flexible wired circuit board formed in a flat-belt sheet-like shape extending in the longitudinal direction. The wired circuit board 1 includes an insulating base layer 2, a conductive pattern 3 formed on the insulating base layer 2, and an insulating cover layer 5 formed on the insulating base layer 2 so as to cover the conductive pattern 3.

Examples of an insulating material used to form the insulating base layer 2 include synthetic resins such as polyimide, polyamideimide, acryl, polyether nitrile, polyether sulfone, polyethylene terephthalate (PET), polyethylene naphthalate, and polyvinyl chloride. Preferably, in terms of heat resistance and a light transmission characteristic, polyimide is used.

As necessary, a pigment or the like is mixed in the insulating material shown above. The pigment is mixed in a proper proportion so as to adjust the reflectance R2 of table reflected light 8 in an inspection step described later.

The insulating base layer 2 is formed in a flat-belt sheet-like shape correspondingly to the outer shape of the wired circuit board 1 extending in the longitudinal direction.

The insulating base layer 2 has a light transmittance T1 in a range of, e.g., not less than 60%, preferably not less than 70%, or more preferably not less than 80%, and normally not more than 100% with respect to light at a wavelength in a range of not less than 500 nm (preferably 500 to 1500 nm, or more preferably 500 to 1000 nm).

When the light transmittance T1 of the insulating base layer 2 is under the range shown above, it may be difficult to set the reflectance R2 (described later) of the table reflected light 8 to a desired range.

The foregoing light transmittance T1 of the insulating base layer 2 can be calculated by forming, separately from the insulating base layer 2 of the wired circuit board 1, a sheet (sheet for base) having generally the same thickness as that of the insulating base layer 2 from the same insulating material as that of the insulating base layer 2, and measuring the light transmittance thereof with a spectrophotometer or the like.

The thickness of the insulating base layer 2 is in a range of, e.g., 5 to 50 μm, or preferably 10 to 40 μm.

Examples of a conductive material used to form the conductive pattern 3 include conductive materials such as copper, nickel, gold, a solder, and an alloy thereof. Preferably, in terms of electric resistance and a light reflection characteristic, copper is used.

The conductive pattern 3 integrally includes wires 6 extending along the longitudinal direction, and arranged in parallel to be spaced apart from each other in the widthwise direction, and terminal portions not shown, but disposed at the both longitudinal end portions of each of the wires 6. Each of the wires 6 is covered with the insulating cover layer 5, while each of the terminal portions not shown is exposed from the insulating cover layer 5. The conductive pattern 3 is formed in a generally rectangular cross-sectional (widthwise cross-sectional) shape.

The thickness of the conductive pattern 3 is in a range of, e.g., 3 to 30 μm, or preferably 5 to 20 μm. The respective widths (widthwise lengths) of the wires 6 and the terminal portions may be the same or different from each other, and are in a range of, e.g., 5 to 500 μm, or preferably 15 to 200 μm. The respective spacings (widthwise spacings) between the individual wires 6 and between the individual terminal portions may be the same or different from each other, and are in a range of, e.g., 5 to 200 μm, or preferably 5 to 100 μm.

The insulating cover layer 5 covers and electrically seals the wires 6. As an insulating material for forming the insulating cover layer 5, the same insulating material as used to form the insulating base layer 2 shown above is used.

The insulating cover layer 5 is formed on the upper surface of the insulating base layer 2 into a pattern covering the wires 6, and exposing the terminal portions. The insulating cover layer 5 covers the upper surface of the base exposed from the conductive pattern 3.

The insulating cover layer 5 has a light transmittance T2 in a range of, e.g., not less than 60%, preferably not less than 70%, or more preferably not less than 80%, and normally not more than 100% with respect to light at a wavelength in a range of not less than 500 nm (preferably 500 to 1500 nm, or more preferably 500 to 1000 nm). The light transmittance T2 of the insulating cover layer 5 may be the same as or different from the light transmittance T1 of the insulating base layer 2, but preferably the same.

When the light transmittance T2 of the insulating cover layer 5 is under the range shown above, it may be difficult to set the reflectance R2 (described later) of the table reflected light 8, a reflectance R1 (described later) of pattern reflected light 7, and a reflectance R3 (described later) of foreign-matter reflected light 9 to desired ranges.

The foregoing light transmittance T2 of the insulating cover layer 5 can be calculated by forming, separately from the insulating cover layer 5 of the wired circuit board 1, a sheet (sheet for cover) having generally the same thickness as that of the insulating cover layer 5 from the same insulating material as that of the insulating cover layer 5, and measuring the light transmittance thereof with a spectrophotometer or the like.

The thickness of the insulating cover layer 5 is in a range of, e.g., 10 to 50 μm, or preferably 14 to 20 μm.

Next, an embodiment of the producing method of the wired circuit board of the present invention is described with reference to FIGS. 2 to 4.

In the method, as shown in FIG. 3, each of the steps (FIGS. 2(a) to 2(d')) in the production of the wired circuit board 1 is performed by, e.g., a roll-to-roll method using a conveying device 13. For example, the conveying device 13 includes a feed-out roll 16 and a wind-up roll 17 which are disposed in mutually spaced-apart relation.

In the roll-to-roll method, e.g., the elongated insulating base layer 2 wound in a roll around the feed-out roll 16 is carried by roll-to-roll conveyance in such a manner as to be fed out toward the wind-up roll 17, and wound up by the wind-up roll 17 for each of the steps. In the course of the roll-to-roll conveyance, the individual steps shown in FIG. 2 are performed in succession.

First, in the method, as shown in FIG. 2(a), the insulating base layer 2 is prepared as a sheet wound around the feed-out roll 16.

Next, in the method, as shown in FIG. 2(b), the conductive pattern 3 is formed in a wired circuit pattern having the wires 6 and the terminal portions on the insulating base layer 2. The conductive pattern 3 is formed by, e.g., a known patterning method such as a subtractive method or an additive method.

Next, in the method, as shown in FIG. 2(c), the insulating cover layer 5 is formed in the foregoing pattern on the insulating base layer 2 so as to cover the conductive pattern 3.

The insulating cover layer 5 is formed by a known method such as, e.g., the application of a resin solution or the adhesion of a resin sheet.

In the application of a resin solution, a photosensitive resin solution (varnish) containing, e.g., a solution of the insulating material mentioned above and a photosensitizer is prepared first. The photosensitive varnish is applied on the entire upper surface of the insulating base layer 2 including the conductive pattern 3, and dried to form a cover coating. Next, the cover coating is exposed to light via a photomask, and developed to be processed into a pattern, and then cured by heating as necessary.

In the adhesion of a resin sheet, a sheet of an insulating material formed in the foregoing pattern in advance is laminated on the insulating base layer 2 and the conductive pattern 3, pressed, and then heated.

In this manner, the wired circuit board 1 (wired circuit board 1 prior to the inspection step) including the insulating base layer 2, the conductive pattern 3 formed thereon, and the insulating cover layer 5 formed on the insulating base layer 2 so as to cover the conductive pattern 3 is prepared.

Thereafter, as shown in FIG. 2(d) or 2(d'), the wired circuit board 1 is placed on a support table 4 (described later), and then the conductive pattern 3 and a foreign matter 11 are inspected (inspection step). In the inspection step, an inspection device 12 shown in FIG. 4 is used.

The inspection device 12 is disposed between the feed-out roll 16 and the wind-up roll 17. The inspection device 12 includes light emitting units 14 and a light receiving unit 15 which are disposed above the wired circuit board 1 conveyed between the feed-out roll 16 and the wind-up roll 17 in the thickness direction of the wired circuit board 1, and also includes the support table 4 disposed below the light emitting units 14 and the light receiving unit 15 in the thickness direction in facing relation thereto.

The light emitting units 14 are disposed in spaced-apart and facing relation in a direction of conveyance. The lower surface of each of the light emitting units 14 facing the wired circuit board 1 serves as a light emitting surface from which a beam of light 10 is emitted. To cause the beams of light 10 emitted from the respective light emitting surfaces to be condensed onto the wired circuit board 1 at a midpoint between the individual light emitting units 14, the light emitting units 14 are disposed in line symmetry to be tilted around a portion where the light beams are condensed (around a condensed light line along the widthwise direction of the wired circuit board 1).

Specifically, each of the light emitting units 14 is, e.g., a lamp capable of emitting the beam of light 10 at a wavelength in a range of not less than 500 nm (preferably 500 to 1500 nm, or more preferably 500 to 1000 nm). Preferably, as a light source, an LED (light emitting diode) capable of emitting light in a wavelength range including those shown above is used.

When the wavelength of the light 10 is within the range shown above, it is possible to increase the light transmittance T1 of the insulating base layer 2 and the light transmittance T2 of the insulating cover layer 5, and set the reflectance R2 (described later) of the table reflected light 8 to a value within a desired range in the inspection step. This allows better-balanced setting of the contrast (described later) between the pattern reflected light 7 and the table reflected light 8 and the contrast (described later) between the table reflected light 8 and the foreign-matter reflected light 9.

The light receiving unit 15 is disposed above the wired circuit board 1 in the thickness direction to be spaced-apart therefrom, and disposed between the individual light emitting units 14 in the direction of conveyance. The lower surface of the light receiving unit 15 serves as a light receiving surface which receives beams of the reflected light 7, 8, and 9 (described later) which are the beams of light 10 reflected by the wired circuit board 1 and the support table 4. The light receiving surface is disposed above the light emitting units 14 so as to face the portion where the light beams are condensed from thereabove.

Specifically, the light receiving unit 15 is formed of, e.g., a near infrared camera, a CCD camera, or the like. Preferably, in terms of versatility, the light receiving unit 15 is formed of a CCD camera, more specifically a CCD line scan camera capable to reading a line (condensed light line) perpendicular to the direction of conveyance of the wired circuit board 1.

The support table 4 has a generally flat-plate shape, and an upper surface (top surface) thereof formed as a flat smooth surface. To set the reflectance R2 of the table reflected light 8 described later to a value within a desired range, a metal material such as, e.g., stainless steel (specifically SUS304 or the like), aluminum, copper, or nickel, a fluorine resin material such as, e.g., polytetrafluoroethylene, or the like is used as a material for forming the support table 4. As necessary, a metal film is formed on the upper surface of the support table 4.

As an example of a material for forming the metal film, the same metal material as used to form the support table 4 shown above is used. As a material for forming the metal film and a metal material for forming the support table 4, different kinds of materials are typically used in combination. The thickness of the metal film is in a range of, e.g., 0.1 to 100 μm.

The support table 4 is disposed below the wired circuit board 1 to be conveyed. The support table 4 has an upper surface thereof in slidable contact with the lower surface of the wired circuit board 1, thereby supporting the wired circuit board 1. The support table 4 is formed with a through hole extending therethrough in the thickness direction, though not shown. To the lower end of the through hole, a compressor is connected.

In the inspection device 12, the angle θ formed between each of the beams of irradiation light 10 emitted from the light emitting units 14 and the reflected light received by the light receiving unit 15 is set to a range of, e.g., not more than 90 degrees, or preferably not more than 45 degrees. The distance between the light emitting surface of each of the light emitting units 14 and the portion of the wired circuit board 1 where the light beams are condensed is set to a range of, e.g., 5 to 300 mm, or preferably 10 to 100 mm. The distance between the portion of the wired circuit board 1 where the light beams are condensed and the light receiving surface of the light receiving unit 15 is set to a range of, e.g., 20 to 300 mm.

Then, by feeding out the wired circuit board 1 wound around the feed-out roll 16 toward the wind-up roll 17 such that the lower surface of the insulating base layer 2 comes into contact with the upper surface of the support table 4, the wired circuit board 1 is placed on the support table 4.

Thereafter, the feed-out operation by the feed-out roll 16 and the wind-up operation by the wind-up roll 17 are interrupted. Then, by activating the compressor to suck in air via the through hole, the wired circuit board 1 is fixed onto the support table 4 (attracted thereto by suction).

Subsequently, the conductive pattern 3 and the foreign matter 11 in the wired circuit board 1 are simultaneously inspected with the inspection device 12.

In the inspection step, the beams of light (irradiation light) 10 at the wavelengths shown above are applied to the wired circuit board 1 from thereabove. Specifically, the beams of light 10 at the wavelengths shown above are emitted from the light emitting units 14 toward the wired circuit board 1.

Through the application of the foregoing light 10, as shown in FIGS. 2(*d*) and 2(*d'*), the pattern reflected light 7 which is the foregoing light 10 reflected by the surface of the conductive pattern 3 via the insulating cover layer 5, the table reflected light 8 which is the foregoing light 10 reflected by the support table 4 via the insulating cover layer 5 and the insulating base layer 2 (insulating base layer 2 between the individual portions of the conductive pattern 3) exposed from the conductive pattern 3, and the foreign-matter reflected light 9 which is the foregoing irradiation light 10 reflected by the foreign matter 11 via the insulating cover layer 5 are sensed by the light receiving unit 15.

The reflectance R1 of the pattern reflected light 7 is in a range of, e.g., not less than 50%, preferably not less than 60%, or more preferably not less than 65%, and normally not more than 100%.

The reflectance R1 of the pattern reflected light 7 is obtained as a ratio (=(Amount of Pattern Reflected Light 7)/(Amount of Irradiation Light 10)×100) of an amount of the pattern reflected light 7 sensed by the light receiving unit 15 to an amount of the irradiation light 10 emitted from the light emitting units 14 when the amount of the irradiation light 10 is assumed to be 100%.

The table reflected light 8 contains, as a primary component thereof, light which is the irradiation light 10 incident on the upper surface of the insulating cover layer 5, downwardly passed through the inside of the insulating cover layer 5, subsequently incident on the upper surface of the insulating base layer 2, downwardly passed through the inside of the insulating base layer 2, reflected by the upper surface of the support table 4, upwardly passed through the inside of the insulating base layer 2 again, subsequently upwardly passed through the inside of the insulating cover layer 5 again, and then emitted from the upper surface of the insulating cover layer 5.

The table reflected light 8 also contains, as secondary components thereof, light (not shown) which is the irradiation light 10 reflected by the upper surface of the insulating cover layer 5 and light (not shown) which is the irradiation light 10 incident on the upper surface of the insulating cover layer 5, reflected by the upper surface (the boundary between the insulating cover layer 5 and the insulating base layer 2) of the insulating base layer 2, upwardly passed through the inside of the insulating cover layer 5 again, and then emitted from the upper surface of the insulating cover layer 5.

The reflectance R2 of such table reflected light 8 is in a range of 25 to 55%, preferably 30 to 50%, or more preferably 35 to 45%.

The reflectance R2 of the table reflected light 8 is obtained as the ratio (=(Amount of Table Reflected Light 8)/(Amount of Irradiation Light 10)×100) of an amount of the table reflected light 8 sensed by the light receiving unit 15 to the amount of the irradiation light 10 emitted from the light emitting units 14 when the amount of the irradiation light 10 is assumed to be 100%.

The reflectance R3 of the foreign-matter reflected light 9 is determined by an insulating material forming the insulating cover layer 5 and by a material forming the foreign matter 11 described later, and is in a range of, e.g., not more than 10%, preferably not more than 5%, or more preferably not more than 1%, and normally not less than 0.2%.

The reflectance R3 of the foreign-matter reflected light 9 is obtained as a ratio (=(Amount of Foreign-Matter Reflected Light 9)/(Amount of Irradiation Light 10)×100) of an amount of the foreign-matter reflected light 9 sensed by the light receiving unit 15 to the amount of the irradiation light 10 emitted from the light emitting units 14 when the amount of the irradiation light 10 is assumed to be 100%.

The foreign-matter reflected light 9 is the irradiation light 10 incident on the upper surface of the insulating cover layer 5, downwardly passed through the inside of the insulating cover layer 5, reflected by the surface of the foreign matter 11, upwardly passed through the inside of the insulating cover layer 5 again, and then emitted from the upper surface of the insulating cover layer 5.

As shown in FIG. 2(*d'*), in the wired circuit board 1 which is determined to be a defective product, the foreign matter 11 is present on the upper surface of the insulating base layer 2 exposed from the conductive pattern 3, and covered with the insulating cover layer 5. Specifically, the foreign matter 11 is present between the individual portions (between the individual wires 6 adjacent in the widthwise direction) of the conductive pattern 3 or present widthwise outside the conductive pattern 3 (outside the widthwise outermost wires 6). Note that the foreign matter 11 may also be present over the individual portions of the conductive pattern 3 and the upper surface of any of the individual portions of the conductive pattern 3.

The shape of the foreign matter 11 is not particularly limited. A material for forming the foreign matter 11 is not particularly limited, and examples of the material that can be listed include a carbon-based inorganic material (a conductive inorganic material except for a metal material) such as carbon black, carbon nanotube, carbon fiber, or graphite, and an organic material (resin material) such as rubber or an adhesive.

In particular, when the foreign matter 11 formed of a material which impairs the performance (electric signal transmission performance) of the conductive pattern 3 is contained, it is necessary to reliably determine the wired circuit board 1 to be a defective product, and remove the wired circuit board 1 or adds a mark (mark indicative of a defective product) thereto. Accordingly, as a material for forming the foreign matter 11 to be sensed, a conductive inorganic material (except for a metal material) can be particularly listed.

Then, based on the contrast (difference between the amounts of light) between the sensed beams of reflected light 7, 8, and 9 (the pattern reflected light 7, the table reflected light 8, and the foreign-matter reflected light 9), the conductive pattern 3 and the foreign matter 11 are simultaneously inspected.

That is, the respective amounts of the beams of reflected light 7, 8, and 9 that have been sensed by the light receiving unit 15 are each subjected to data processing using a CPU (not shown) or the like connected to the light receiving unit 15 to form image processed views (image processed views obtained when the wired circuit board 1 is viewed in plan view. See FIGS. 6 to 8). In the formed image processed views, the conductive pattern 3, the insulating base layer 2, the insulating cover layer 5, and the foreign matter 11 are depicted so that the conductive pattern 3 and the foreign matter 11 are inspected.

Specifically, as shown in FIGS. 2(d), 2(d'), and 6 to 8, the conductive pattern 3 is inspected based on the contrast between the pattern reflected light 7 and the table reflected light 8.

In the inspection of the conductive pattern 3, data on the conductive pattern 3 is acquired from the contrast between the pattern reflected light 7 and the table reflected light 8, and image processed views are formed using the CPU. From such image processed views, the pattern shape of the conductive pattern 3 is correctly recognized so that a defect in the wires 6 or the terminal portions, a short circuit between the wires 6 or between the terminal portions, and the like are accurately determined.

The contrast between the pattern reflected light 7 and the table reflected light 8 is a difference D1 between the respective reflectances thereof and, more specifically, the value D1 (=R1−R2) obtained by subtracting the reflectance R2 of the table reflected light 8 from the reflectance R1 of the pattern reflected light 7, which is in a range of, e.g., not less than 20%, or preferably not less than 30%, and normally not more than 70%. In other words, the reflectance R1 of the pattern reflected light 7 is higher than the reflectance R2 of the table reflected light 8 by a value of, e.g., not less than 20%, or preferably not less than 30%.

When the contrast between the pattern reflected light 7 and the table reflected light 8 is within the range shown above, it is possible to more accurately determine whether or not the shape of the conductive pattern 3 is defective.

In the inspection of the conductive pattern 3 described above, when the data on the pattern acquired from the contrast between the pattern reflected light 7 and the table reflected light 8 is obtained as data on a pattern which is not present in the data on the conductive pattern 3 as shown in FIG. 2(d'), it is determined that the shape of the conductive pattern 3 is defective (the wires 6 are short-circuited). On the other hand, when there is no difference between the data on the pattern acquired from the contrast between the pattern reflected light 7 and the table reflected light 8 and the original data on the conductive pattern 3 as shown in FIG. 2(d), it is determined that the shape of the conductive pattern 3 is normal.

As shown in FIGS. 2(d), and 6 to 8, the foreign matter 11 is inspected based on the contrast between the table reflected light 8 and the foreign-matter reflected light 9.

In the inspection of the foreign matter 11, data on the pattern of each of the insulating base layer 2 exposed from the conductive pattern 3 and the insulating cover layer 5 covering the upper surface thereof is acquired from the contrast between the table reflected light 8 and the foreign-matter reflected light 9, and an image processed view is formed using the CPU. From such an image processed view, the pattern shape of each of the insulating base layer 2 exposed from the conductive pattern 3 and the insulating cover layer 5 covering the upper surface thereof is correctly recognized, and the presence or absence of the foreign matter 11 is accurately determined.

The contrast between the table reflected light 8 and the foreign-matter reflected light 9 is a difference D2 between the respective reflectances thereof and, more specifically, the value D2 (=R2−R3) obtained by subtracting the reflectance R3 of the foreign-matter reflected light 9 from the reflectance R2 of the table reflected light 8, which is in a range of, e.g., not less than 20%, or preferably not less than 30%, and normally not more than 70%. In other words, the reflectance R2 of the table reflected light 8 is higher than the reflectance R3 of the foreign-matter reflected light 9 by a value of, e.g., not less than 20%, or preferably not less than 30%.

In the inspection of the foreign matter 11 described above, when the data on the pattern acquired from the contrast between the table reflected light 8 and the foreign-matter reflected light 9 is obtained as data on a pattern which is not present in the data on the pattern of each of the insulating base layer 2 exposed from the conductive pattern 3 and the insulating cover layer 5 covering the upper surface thereof as shown in FIG. 2(d'), it is determined that the foreign matter 11 is present on the upper surface of the insulating base layer 2 exposed from the conductive pattern 3, and covered with the insulating cover layer 5.

On the other hand, when there is no difference between the data on the pattern acquired from the contrast between the table reflected light 8 and the foreign-matter reflected light 9 and the original data on the pattern of each of the insulating base layer 2 exposed from the conductive pattern 3 and the insulating cover layer 5 covering the upper surface thereof, it is determined that the foreign matter 11 is not present on the upper surface of the insulating base layer 2 exposed from the conductive pattern 3, and not covered with the insulating cover layer 5.

Note that the inspection using the beams of light 10 at the wavelengths shown above is usually performed at a room temperature (25° C.), and the temperature of the surface of the wired circuit board 1 (the surface of the insulating cover layer 5) after the inspection is, e.g., a room temperature, not more than 30° C., or preferably not more than 25° C. That is, the range of the temperature rise of the wired circuit board 1 observed after the inspections of the conductive pattern 3 and the foreign matter 11 is, e.g., not more than 5° C.

Subsequently, in the method, the suction by the compressor is terminated to unfix the wired circuit board 1 from the support table 4, and then the conveyance of the wired circuit board 1 by the conveying device 13 is resumed. As a result, the wired circuit board 1 after the inspection step is wound up by the wind-up roll 17, while the wired circuit board 1 prior to the inspection step is newly fed out from the feed-out roll 16, placed on the support table 4, and fixed thereto. Thereafter, the same inspection step as described above is performed. In the inspection device 12, such an inspection step is repeated.

Thereafter, the wired circuit board 1 wound up by the wind-up roll 17, and determined to be a defective product is removed by cutting it off from the elongated insulating base layer 2 or marked, while the wired circuit board 1 determined to be a non-defective product is accepted.

In accordance with the method, in the inspection step for the conductive pattern 3 and the foreign matter 11, the reflectance R2 of the table reflected light 8 is in a range of 25 to 55%, and the reflectance R3 of the foreign-matter reflected light 9 is in a range of not more than 10%.

This allows each of the contrast between the pattern reflected light 7 and the table reflected light 8 and the contrast between the table reflected light 8 and the foreign-matter reflected light 9 to be set high in a well-balanced manner.

Therefore, it is possible to easily and simultaneously perform the inspection of the conductive pattern 3 and the inspection of the foreign matter 11 present on the upper surface of the insulating base layer 2 exposed from the conductive pattern 3.

In the description given above, the roll-to-roll method has been shown as an example of the producing method of the wired circuit board of the present invention. However, the producing method of the wired circuit board of the present invention is not limited thereto. For example, it is possible to use a single-wafer method or the like, though not shown.

In the description given above, the flexible wired circuit board in which the insulating base layer 2 is not supported by a metal supporting layer or the like is shown as an example of the wired circuit board obtained by the producing method of the wired circuit board of the present invention. However, the producing method of the wired circuit board of the present invention is widely applicable to the production of various wired circuit boards such as, e.g., a flexible wired circuit board in which the lower surface of the peripheral end portion of the insulating base layer 2 is supported by a metal supporting layer, and the metal supporting layer is provided as a reinforcing layer, a COF board (including a TAB tape carrier or the like), and a suspension board with circuit.

EXAMPLES

Hereinbelow, the present invention is described more specifically by showing the examples and comparative examples thereof. However, the present invention is by no means limited to the examples and the comparative examples.

Example 1

By a roll-to-roll method using the conveying device shown in FIG. 3 described above, the following steps were performed in succession to produce a flexible wired circuit board.

That is, an insulating base layer made of polyimide (A) and in the shape of an elongated sheet having a width of 300 mm and a thickness of 12.5 μm was prepared (see FIG. 2(*a*)).

Then, on the insulating base layer, a conductive pattern made of copper and having a thickness of 8 μm was formed in a wired circuit pattern having wires and terminal portions by an additive method (see FIG. 2(*b*)). The width of each of the wires was 30 μm. The width of each of the terminal portions was 30 μm. The spacing between the individual wires was 60 μm. The widthwise spacing between the individual terminal portions was 60 μm.

Then, carbon black (foreign matter) having an average particle diameter of 20 μm was mixed onto the insulating base layer exposed from the wires.

Then, a varnish of a photosensitive polyamic acid resin was applied on the entire upper surface of the insulating base layer including the conductive pattern and the foreign matter, dried, exposed to light, developed to be processed into the foregoing pattern, and then cured by heating to form an insulating cover layer made of the polyimide (A) and having a thickness of 12.5 μm (see FIG. 2(*c*)).

In this manner, the flexible wired circuit board was prepared.

Then, as shown in FIG. 4 described above, the carbon black and the conductive pattern were simultaneously inspected using an inspection device including light emitting units (light sources: LEDs for diffused illumination), a light receiving unit (CCD line scan camera, Model No. P3-80-12K40 commercially available from DALSA, Inc.), and a support table (made of stainless steel (SUS304)) having a tin film having a thickness of 0.5 μm formed on the surface thereof (see FIGS. 2(*d*) and 2(*d'*)).

In the inspection device, the angle formed between a light beam emitted from each of the light emitting units and light received by the light receiving unit was 10 degrees, the distance between the light emitting surface of each of the light emitting units and the portion of the flexible wired circuit board where the light beams were condensed was 50 mm, and the distance between the light receiving surface of the light receiving unit and the portion of the flexible wired circuit board where the light beams were condensed was 120 mm.

This inspection was performed using light at a wavelength of 670 nm at a temperature of 25° C.

An image processed view obtained by data processing is shown in FIG. 6, and evaluation in the inspection is shown in Table 1.

Separately from the flexible wired circuit board, sheets each made of the polyimide (A), which was the same material as those of the insulating base layer and the insulating cover layer, and having a thickness of 12.5 μm were formed as a sheet for base and a sheet for cover, and the light transmittances (T1 and T2) of the sheets at a wavelength of 670 nm were measured with a spectrophotometer (UV-VIS-NIR spectrophotometer commercially available from JASCO Corporation under the tradename of V-670). The result of the measurement is shown in Table 1.

Example 2

An inspection step was performed in the same manner as in EXAMPLE 1 except that an inspection device including a support table having a surface thereof formed with a copper film having a thickness of 0.5 μm instead of the tin film was used in the inspection step.

An image processed view obtained by data processing is shown in FIG. 7, and evaluation in the inspection is shown in Table 1.

Example 3

A flexible wired circuit board was prepared in the same manner as in EXAMPLE 1 except that, in the preparation of the flexible wired circuit board, the material and thickness of the insulating base layer were changed to polyimide (B) and 18 μm, and the material and thickness of the insulating cover layer were changed to the polyimide (B) and 18 μm.

Then, the inspection step was performed in the same manner as in EXAMPLE 1 except that, in the inspection step, an inspection device including a support table having a surface thereof formed with a copper film having a thickness of 0.5 μm instead of the tin film was used, and light at a wavelength of 720 nm was used instead of the light at a wavelength of 670 nm.

An image processed view obtained by data processing is shown in FIG. 8, and evaluation in the inspection is shown in Table 1.

Separately from the flexible wired circuit board, sheets each made of the polyimide (B), which was the same material as those of the insulating base layer and the insulating cover layer, and having a thickness of 18 μm were formed as the sheet for base and the sheet for cover, and the light transmittances (T1 and T2) of the sheets at a wavelength of 720 nm were measured with a spectrophotometer (UV-VIS-NIR spectrophotometer commercially available from JASCO Corporation under the tradename of V-670). The result of the measurement is shown in Table 1.

Comparative Example 1

A flexible wired circuit board was prepared in the same manner as in EXAMPLE 1 except that, in the preparation of the flexible wired circuit board, the material and thickness of the insulating base layer were changed to polyimide (C) and 10 μm, and the material and thickness of the insulating cover layer were changed to the polyimide (C) and 10 μm.

Then, the inspection step was performed in the same manner as in EXAMPLE 1 except that, in the inspection step, an inspection device including a support table having a surface thereof formed with a nickel film having a thickness of 0.5 μm instead of the tin film was used, and light at a wavelength of 970 nm was used instead of the light at a wavelength of 670 nm.

An image processed view obtained by data processing is shown in FIG. 9, and evaluation in the inspection is shown in Table 1.

Separately from the flexible wired circuit board, sheets each made of the polyimide (C), which was the same material as those of the insulating base layer and the insulating cover layer, and having a thickness of 10 μm were formed as the sheet for base and the sheet for cover, and the light transmittances (T1 and T2) of the sheets at a wavelength of 970 nm were measured with a spectrophotometer (UV-VIS-NIR spectrophotometer commercially available from JASCO Corporation under the tradename of V-670). The result of the measurement is shown in Table 1.

Comparative Example 2

A flexible wired circuit board was prepared in the same manner as in EXAMPLE 1 except that, in the preparation of the flexible wired circuit board, a nickel plating layer having a thickness of 0.5 μm was further formed on the surface of the conductive pattern.

Then, the inspection step was performed in the same manner as in EXAMPLE 1 except that, in the inspection step, an inspection device including a support table having a surface thereof formed with a copper film having a thickness of 0.5 μm instead of the tin film was used, and light at a wavelength of 970 nm was used instead of the light at a wavelength of 670 nm.

An image processed view obtained by data processing is shown in FIG. 10, and evaluation in the inspection is shown in Table 1.

Separately from the flexible wired circuit board, sheets each made of the polyimide (A), which was the same material as those of the insulating base layer and the insulating cover layer, and having a thickness of 12.5 μm were formed as the sheet for base and the sheet for cover, and the light transmittances (T1 and T2) of the sheets at a wavelength of 970 nm were measured with a spectrophotometer (UV-VIS-NIR spectrophotometer commercially available from JASCO Corporation under the tradename of V-670). The result of the measurement is shown in Table 1.

Comparative Example 3

A flexible wired circuit board was prepared in the same manner as in EXAMPLE 1 except that, in the preparation of the flexible wired circuit board, the material and thickness of the insulating base layer were changed to the polyimide (C) and 10 μm, and a nickel plating layer having a thickness of 0.5 μm was further formed on the surface of the conductive pattern.

Then, the inspection step was performed in the same manner as in EXAMPLE 1 except that, in the inspection step, a support table (made of stainless steel (SUS304)) having a surface thereof not formed with the tin film was used, and light at a wavelength of 850 nm was used instead of the light at a wavelength of 670 nm.

An image processed view obtained by data processing is shown in FIG. 11, and evaluation in the inspection is shown in Table 1.

Separately from the flexible wired circuit board, sheets each made of the polyimide (C), which was the same material as those of the insulating base layer and the insulating cover layer, and having a thickness of 10 μm were formed as the sheet for base and the sheet for cover, and the light transmittances (T1 and T2) of the sheets at a wavelength of 850 nm were measured with a spectrophotometer (UV-VIS-NIR spectrophotometer commercially available from JASCO Corporation under the tradename of V-670). The result of the measurement is shown in Table 1.

Table 1

TABLE 1

| | | Examples/Comparative Examples | | | | | |
|---|---|---|---|---|---|---|---|
| | | Example 1 | Example 2 | Example 3 | Comparative Example 1 | Comparative Example 2 | Comparative Example 3 |
| Material | Surface of Conductive Pattern | Copper | Copper | Copper | Copper | Nickel | Nickel |
| | Base Insulating Layer/ Cover Insulating Layer | Polyimide (A) | Polyimide (A) | Polyimide (B) | Polyimide (C) | Polyimide (A) | Polyimide (C) |

TABLE 1-continued

| | | Examples/Comparative Examples | | | | | |
|---|---|---|---|---|---|---|---|
| | | Example 1 | Example 2 | Example 3 | Comparative Example 1 | Comparative Example 2 | Comparative Example 3 |
| | Surface of Support Table | Tin | Copper | Copper | Nickel | Copper | Stainless Steel |
| Light Transmittance (%) | Base Insulating Layer (T1) Cover Insulating Layer (T2) | 83 | | 72 | 72 | 88 | 63 |
| Wavelength of Irradiation Light (nm) | | 670 | 670 | 720 | 970 | 970 | 850 |
| Reflectance (%) | Pattern Reflected Light (R1) | 65 | 65 | 50 | 50 | 40 | 20 |
| | Table Reflected Light (R2) | 35 | 45 | 25 | ≦15 | 60 | ≦10 |
| | Foreign-Matter Reflected Light (R3) | ≦5 | ≦5 | ≦5 | ≦5 | ≦5 | ≦5 |
| Inspection | Foreign Matter | Successfully Inspected | Successfully Inspected | Successfully Inspected | Unsuccessfully Inspected | Successfully Inspected | Unsuccessfully Inspected |
| | Conductive Pattern | Successfully Inspected | Successfully Inspected | Successfully Inspected | Successfully Inspected | Unsuccessfully Inspected | Unsuccessfully Inspected |

In the row showing the results of the inspections of the foreign matter of Table 1, "Successfully Inspected" indicates that the presence of the foreign matter between the individual portions of the conductive pattern could be definitely determined, and "Unsuccessfully Inspected" indicates that the presence or absence of the foreign matter between the individual portions of the conductive pattern could not be definitely determined. In the row showing the results of the inspections of the conductive pattern, "Successfully Inspected" indicates that the normal shape of the conductive pattern could be definitely determined, and "Unsuccessfully Inspected" indicates that whether or not the shape of the conductive pattern was defective could not be determined.

While the illustrative embodiments of the present invention are provided in the above description, such is for illustrative purpose only and it is not to be construed limitative. Modification and variation of the present invention that will be obvious to those skilled in the art is to be covered by the following claims.

What is claimed is:

1. A producing method of a wired circuit board, the producing method comprising the steps of:
   preparing the wired circuit board comprising an insulating base layer, a conductive pattern formed on the insulating base layer, and an insulating cover layer formed on the insulating base layer so as to cover the conductive pattern;
   placing the wired circuit board on a support table; and
   applying light from above the wired circuit board toward the wired circuit board, and sensing pattern reflected light which is the light reflected by the conductive pattern via the insulating cover layer, table reflected light which is the light reflected by the support table via the insulating cover layer and the insulating base layer exposed from the conductive pattern, and foreign-matter reflected light which is the light reflected by a foreign matter present on the insulating base layer exposed from the conductive pattern to inspect the conductive pattern and the foreign matter based on a contrast therebetween, wherein,
   in the step of inspecting the conductive pattern and the foreign matter, a reflectance of the table reflected light is in a range of 25 to 55%, and a reflectance of the foreign-matter reflected light is in a range of not more than 10%.

2. The producing method of the wired circuit board according to claim 1, wherein a light transmittance of each of the insulating base layer and the insulating cover layer is not less than 60%.

3. The producing method of the wired circuit board according to claim 1, wherein a reflectance of the pattern reflected light is higher than the reflectance of the table reflected light by a value of not less than 20%.

4. The producing method of the wired circuit board according to claim 1, wherein a wavelength of the light is in a range of not less than 500 nm.

* * * * *